United States Patent [19]

Kamienski et al.

[11] Patent Number: 5,145,600
[45] Date of Patent: Sep. 8, 1992

[54] LOW VISCOSITY HYDROCARBON SOLUTION OF DIALKYLMAGNESIUM COMPOUNDS

[75] Inventors: Conrad W. Kamienski, Gastonia; B. Troy Dover, Kings Mountain, both of N.C.

[73] Assignee: FMC Corporation, Philadelphia, Pa.

[21] Appl. No.: 391,811

[22] Filed: Aug. 9, 1989

Related U.S. Application Data

[63] Continuation-in-part of Ser. No. 160,425, Feb. 25, 1988, abandoned.

[51] Int. Cl.$^5$ ................................. C09K 3/00
[52] U.S. Cl. ........................... 252/182.3; 252/183.11; 502/115; 502/153
[58] Field of Search ............ 252/182.3, 183.11; 502/153, 115

[56] References Cited

U.S. PATENT DOCUMENTS

| | | | |
|---|---|---|---|
| 3,737,393 | 6/1973 | Sittard | 252/131 |
| 3,742,077 | 6/1973 | Kamienski et al. | 260/668 B |
| 3,822,219 | 7/1974 | Kamienski et al. | 252/431 |
| 3,847,883 | 11/1974 | Kamienski et al. | 260/83.7 |
| 4,069,267 | 1/1978 | Kamienski et al. | 260/665 |
| 4,127,507 | 11/1978 | Fannin et al. | 252/431 |
| 4,207,207 | 6/1980 | Sanchez et al. | 252/431 |
| 4,222,969 | 9/1980 | Fannin et al. | 260/665 |
| 4,283,515 | 8/1981 | Gibbs | 526/127 |
| 4,299,781 | 11/1981 | Fannin et al. | 260/665 |
| 4,355,016 | 6/1982 | Dombro | 252/429 |
| 4,396,554 | 8/1983 | Robinson | 260/665 |
| 4,455,387 | 6/1984 | McKinnie et al. | 502/153 |
| 4,529,715 | 7/1985 | Fuentes et al. | 502/115 |
| 4,547,477 | 10/1985 | Malpass et al. | 502/153 |
| 4,678,614 | 7/1987 | Kamienski et al. | 260/665 |
| 4,707,462 | 11/1987 | Malpass et al. | 502/115 |
| 4,820,672 | 4/1989 | Mehta | 502/115 |
| 4,944,894 | 7/1990 | Mehta et al. | 252/182.3 |

*Primary Examiner*—Edward A. Miller

[57] ABSTRACT

This invention concerns an improved process for preparing a hydrocarbon soluble dialkylmagnesium compound by reacting a dialkylmagnesium-magnesium chloride composition in an inert hydrocarbon solvent with a chemical selected from an alkali metal alkyl compound and an alkali metal trialkylmagnesiate compound and dialkylmagnesium compounds of the formula $$MgR_aR^1_bR^2_cR^3_dR^4_e$$

wherein $a+b+c+d=2$, R is a 2-alkylsubstituted primary alkyl group and $R^1$, $R^2$, $R^3$ and $R^4$ are hydrocarbyl groups which may be the same or different.

3 Claims, No Drawings

LOW VISCOSITY HYDROCARBON SOLUTION OF DIALKYLMAGNESIUM COMPOUNDS

This application is a continuation-in-part of application Ser. No. 160,425, filed Feb. 25, 1988, now abandoned.

This invention concerns a process for preparing novel hydrocarbon-soluble dialkylmagnesium compounds, sometimes named magnesium alkyls to mimic aluminum alkyl terminology.

Magnesium alkyls have been in commercial usage for not much over a dozen years although their preparation was described many years before. Dialkylmagnesium compounds have their major utility as precursors for the preparation of catalysts useful in olefin polymerization, see U.S. Pat. Nos. 4,529,715; 4,283,515; and 4,335,016. They have also found utility as components of polymerization catalyst and initiator compositions useful for the polymerization and telomerization of 1,3-dienes, see U.S. Pat. Nos. 3,742,077; 3,822,219; 3,847,883.

The main methods of preparation of dialkylmagnesium compounds are described in recent overview articles, see D. B. Malpass in Kirk Othmer, Encycl. Chem. Tech., Vol. 16, 3rd Ed., pp. 558-562 (1981) J. Wiley; W. E. Lindsell in Comprehensive Organometallic Chemistry, Vol. 1, pp. 198-201, Pergamon Press (1982). These methods include (a) direct preparation from magnesium metal and an alkyl halide (usually chloride), (b) further reaction of such a product mixture as produced by method (a) with an alkyllithium compound of the $\alpha$-branched type, i.e., a secondary or tertiary alkyllithium (RLi), (c) reaction of magnesium chloride with said secondary or tertiary alkyllithium compound, and (d) reaction of sec-butyllithium with sec-butylmagnesium chloride in ether with subsequent removal of ether.

Generally, it is known that to achieve significant hydrocarbon solvent solubility of such dialkylmagnesium compounds, it is necessary to do one of the following: (i) In process (a) above, use alkyl chlorides of $C_5$ chain length or higher—see Glaze & Selman, J. Organometal. Chem., 5, (1966) 477-480, and L. I. Zakharkin et al., Tetrahedron Letters, 14, 631-633 (1962); (ii) In process (a) above, use mixtures of linear chain $C_1$-$C_4$ alkyl chlorides, see D. B. Malpass et al., U.S. Pat. No. 4,127,507, U.S. Pat. No. 4,207,207, and U.S. Pat. No. 4,222,969; (iii) In process (a) above, use mixtures of linear chain $C_1$-$C_4$ lower alkyl chlorides and $C_5$ and higher alkyl chlorides, see C. W. Kamienski et al., U.S. Pat. No. 4,069,267; (iv) In process (a) above, use mixtures of linear and "remote" branched chain alkyl chlorides, see G. C. Robinson and B. G. McKinnie U.S. Pat. No. 4,396,554; (v) In process (b) above, use $\alpha$-branched (e.g., secondary and tertiary butyl) alkyl chlorides to react with by-product $MgCl_2$ in the presence of linear alkylmagnesium compounds, see C. W. Kamienski et al., U.S. Pat. No. 4,069,267; (vi) In process (c) above, react anhydrous "activated" $MgCl_2$ with two equivalents of sec-butyllithium, see C. W. Kamienski and J. F. Eastham, J. Org. Chem., 34, 4, 1116 (1969); (vii) carry out process (d) above; (viii) React magnesium metal with ethylene and an alkyl halide to form an alkylmagnesium composition which in solution contains at least four different alkyl groups, B. G. McKinnie and G. C. Robinson, U.S. Pat. No. 4,455,387.

Unfortunately, in all but processes (iii), (v), (vi), and (vii) there is loss of at least half the magnesium metal utilized in the processes to magnesium chloride, while in said processes (iii), (v), (vi), and (vii), expensive lithium alkyl must be used to convert the by-product magnesium chloride to a useful dialkyl-magnesium compound.

It is well known that trialkylaluminum compounds reduce the viscosity of linear (unbranched) dialkylmagnesium compounds (U.S. Pat. No. 3,737,393). References dealing with reduction of solution viscosity of dialkyl-magnesium compounds by various other agents are described by B. Malpass and co-workers in U.S. Pat. Nos. 4,299,781 and 4,547,477.

Unfortunately, in all but processes (iii), (v), (vi), and (vii) above, the viscosity of the resulting dialkylmagnesium solutions is so high as to warrant handling of the products very difficult, thus necessitating the addition of 2-3 mole % aluminum as either trialkylaluminum or trialkoxyaluminum in order to reduce viscosity. It is noteworthy that, in the use of dialkylmagnesium and magnesium alkoxide solutions to prepare catalysts for the polymerization of olefins, it is advantageous to have little or preferably no aluminum alkyl or aluminum alkoxide present where these solutions are used to generate magnesium chloride carriers for titanium-bearing polyolefin catalysts, as the resulting magnesium chloride crystallites are contaminated with aluminum chloride. On subsequent treatment of the resulting catalyst with an aluminum alkyl co-catalyst, the occluded aluminum chloride can be leached out, thus causing degradation of the magnesium chloride crystal lattice and leading to undesirable changes in the selectivity of the catalyst, and in some cases to a catalyst not as efficient as others in polymerizing olefins into polyolefins.

With the foregoing in mind, it is an object of the present invention to provide an improved process for producing a dialkylmagnesium compound.

It is a further object of the invention to provide an improved process as noted above which avoids the loss of magnesium in the reaction to products other than dialkylmagnesium.

Still another object of the present invention is to provide dialkylmagnesium solutions in hydrocarbon solvents which are low in viscosity in the absence of aluminum compounds.

The present invention provides an improved process for producing hydrocarbon solutions of dialkylmagnesium compounds, containing a mixture of two or more different alkyl groups, having improved solubility and viscosity characteristics. This new process reacts an alkali metal trialkylmagnesiate, in which magnesiate at least one alkyl group is a $C_4$-$C_{18}$ 2-alkyl substituted alkyl group, with a mixture of a magnesium halide and a dialkylmagnesium compound that is derived from the reaction of magnesium metal with a $C_1$ to $C_{18}$ linear or a $C_5$ to $C_{18}$ remotely branched alkyl halide. These improved dialkylmagnesium compounds containing 2-alkyl substituted alkyl groups have improved solubility and viscosity characteristics when compared to comparable dialkylmagnesium compounds containing only linear or remotely branched alkyl groups.

The expression dialkylmagnesium compound as used herein includes substances which are mixtures of compounds. The term compound is used in its usual sense; that is, compounds are substances that are composed of two or more elements in fixed proportions whereas compositions are mixtures of two or more compounds.

The compositions produced by the process of the present invention contain a mixture of dialkylmagnesium compounds which, in accord with the law of definite proportions, contain two alkyl groups per magnesium atom. However, the compounds are in solution in a solvent so that the alkyl groups of two or more different dialkylmagnesium compounds are free to interchange with each other. The process generally contemplates a selection of reactants so as to provide up to four or more different alkyl groups in solution; the compounds always contain at least two different alkyl groups. Hence, the products of the process are solutions of dialkylmagnesium compounds that contain two or more different alkyl groups in the proportion of two alkyl groups per magnesium atom, but in which solutions the alkyl groups are freely interchanging (equilibrating) with each other. Compounds produced by the process of the invention include, but are not limited to, n-butyl-2-ethylhexylmagnesium; a mixture of n-butyl-, n-hexylmagnesium and bis-2-ethylhexylmagnesium; a mixture of n-butyl-, n-octylmagnesium and bis-2-ethylhexylmagnesium, and the like. The mixtures can be expressed as a single equilibrated magnesium compound, with the total of alkyl groups equalling two per magnesium atom. Where there are more than two different alkyl groups per magnesium atom, it is understood that they are present in fractional amounts. Thus, a mixture of n-butyl-n-octyl magnesium and bis-2-ethylhexylmagnesium can be expressed as n-butyl-n-octyl-2-ethylhexylmagnesium. While solutions of compounds containing four or more different alkyl groups are within the scope of the invention, two or three different alkyl groups are considered more typical.

The alkali metal trialkylmagnesiate reactant of our invention can be prepared separately or in situ. It is well known that alkali metal trialkylmagnesiates are produced by simultaneously adding to a stirred dispersion of an alkali metal in an inert liquid hydrocarbon solvent a soluble dialkylmagnesium compound and an alkyl halide. For example, see U.S. Pat. No. 4,678,614. Thus, it is convenient to separately prepare the alkali metal trialkylmagnesiate and add it to a mixture of a magnesium halide and dialkylmagnesium compound derived from the the reaction of magnesium metal with a linear or remotely branched alkyl halide. Such dialkylmagnesium compounds are hydrocarbon insoluble or if soluble are very viscous. Preferably, the process is conducted in a single reactor by reacting a linear or remotely branched alkyl halide with magnesium metal in an inert liquid hydrocarbon to produce a mixture of magnesium halide and linear or remotely branched dialkylmagnesium in the hydrocarbon medium to which mixture is added a dispersion of alkali metal after which a 2-alkyl substituted alkyl halide is slowly added to the reaction mixture containing the alkali metal dispersion, dialkylmagnesium compound and magnesium halide to complete the reaction sequence. The preferred alkyl halides are alkyl chlorides.

The improved processes to prepare dialkylmagnesium compounds can be represented in equation form as follows (wherein, for process (a), M=Alkali metal; $R^1$, $R^2$, $R^3$ and $R^4$ are the same or independently selected normal, secondary or tertiary alkyl groups and R is a 2-alkyl substituted alkyl group); for process (b), $R^1$ and $R^2$ are the same or independently selected normal linear or remotely branched (3-or higher alkyl-substituted) alkyl groups, and R is 2-alkyl substituted alkyl group.

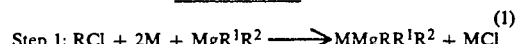

Process (a)

$$\text{Step 1: } RCl + 2M + MgR^1R^2 \longrightarrow MMgRR^1R^2 + MCl \quad (1)$$

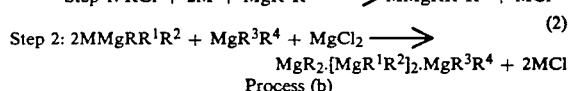

$$\text{Step 2: } 2MMgRR^1R^2 + MgR^3R^4 + MgCl_2 \longrightarrow$$
$$MgR_2 \cdot [MgR^1R^2]_2 \cdot MgR^3R^4 + 2MCl \quad (2)$$

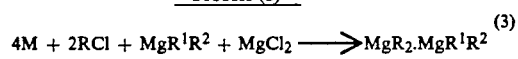

Process (b)

$$4M + 2RCl + MgR^1R^2 + MgCl_2 \longrightarrow MgR_2 \cdot MgR^1R^2 \quad (3)$$

Processes (a) and (b) are both conducted in a hydrocarbon medium. Process (b) essentially incorporates both steps of process (a), albeit with the use of only a single dialkylmagnesium compound type. When M in Process (a) is sodium and $R^1$ is a 2-ethylhexyl group Step 1 of Process (a) produces a sodium trialkylmagnesiate containing a 2-alkyl substituted alkyl group along with by-product sodium chloride which is separated. The sodium trialkylmagnesiate $MMgRR^1R^2$ from Step 1 is then reacted with a mixture of magnesium chloride and a dialkylmagnesium compound derived from the reaction of magnesium metal with either a linear or a remotely branched substituted alkyl chloride or mixtures of such alkyl chlorides. Thus, Step 2 of Process (a) produces a mixture of dialkylmagnesium compounds which is represented by the formula $MgR_2.R^1MgR^2.MgR^3R^4$ and additional by-product sodium chloride. Use of mixtures of alkyl chlorides (as in Examples 2 and 4) produces products containing a mixture containing more than two different alkyl groups in an interchanged or equilibrated product. Use of mixtures of dialkylmagnesium compounds produces similar interchanged or equilibrated products.

In process (a) a solution of sodium trialkylmagnesiate, as prepared in Step 1 (M=sodium), is added to a mixture of dialkylmagnesium and magnesium chloride generally prepared in a prior step from magnesium metal and an alkyl halide in a hydrocarbon solvent (Step 2). A portion of the resulting separated equilibrated mixture of dialkylmagnesium compounds in solution may then be recycled to Step 1 to reform sodium trialkylmagnesiate, which latter product is then further reacted with another separately prepared dialkylmagnesium/magnesium chloride mixture as in Step 2 to form more of the desired dialkylmagnesium compound mixture.

In process (b) the desired alkyl halide (an RCl such as a 2-alkyl substituted alkyl chloride) is added to a mixture of finely divided sodium metal and a dialkylmagnesium compound-magnesium chloride mixture (generally prepared in the same pot in a prior step from magnesium metal and an alkyl chloride in a hydrocarbon solvent), or both alkyl halide (RCl) and dialkylmagnesium-magnesium chloride mixture are added simultaneously to the sodium dispersion. The products of both processes (a) and (b), clear solutions of dialkylmagnesium compounds in hydrocarbon solvents, are separated by filtration.

Obviously, it is possible to directly react a preformed sodium alkyl (no "carrier" $R_2Mg$ present) with a mixture of dialkylmagnesium and magnesium chloride (as generated from the reaction of magnesium metal and an alkyl chloride) to obtain the desired novel dialkylmagnesium compounds directly. However, as has been stated above and shown in U.S. Pat. No. 4,678,614, such a process leads to generally poorer yields of a highly unstable sodium alkyl which becomes discolored and undesired solids are formed within a relatively short time after its preparation.

A particularly advantageous and desirable aspect of the process of this invention is that it can be carried out in the absence of aromatic hydrocarbon solvents or Lewis bases with high yields and good stability of the resulting dialkylmagnesium product. Where solubility and viscosity properties are particularly important, it is preferred to use as the alkyl halide of process (a) Step 1 and process (b) a 2-alkyl substituted $C_4$-$C_{18}$ saturated acyclic primary alkyl chloride. This produces dialkylmagnesium solution product with excellent solubility, good thermal stability, and low viscosity. These compounds cannot be obtained by the prior art processes since dialkylmagnesium compounds derived from $C_4$-$C_{18}$ 2-alkyl substituted saturated acyclic primary alkyl halides cannot be directly prepared using magnesium metal in purely hydrocarbon solvents. The reaction product of sodium, a 2-alkyl substituted alkyl chloride and magnesium chloride is necessary to obtain the desired 2-alkyl substituted magnesium compound.

Thus, the processes of the present invention may be employed to produce a novel class of dialkylmagnesium compositions containing at least one 2-alkyl-substituted saturated acyclic primary alkyl group. These compositions are characterized by excellent solubility and low viscosity in a liquid aliphatic or cycloaliphatic solvent in the absence of aromatic solvents, Lewis bases, or aluminum compounds. They are especially useful in applications where the presence of such substances is undesirable such as in the preparation of olefin polymerization catalysts.

The novel dialkylmagnesium compositions of the present invention may be represented by the formula $$MgR_aR^1_bR^2_cR^3_dR^4_e$$

where $a=0.5$ to 1.9; b, c, d, and $e=0.1$ to 1.5; and $a+b+c+d+e=2$. R is a 2-alkylsubstituted $C_4$-$C_{18}$ alkyl, and $R^1$, $R^2$, $R^3$, and $R^4$ are $C_1$ to $C_{18}$ linear, or $C_5$-$C_{18}$ remotely branched alkyl groups which may be the same or different. These dialkylmagnesium compositions may be provided in the form of a solution in a solvent consisting essentially of liquid aliphatic and/or cycloaliphatic solvents in the absence of aromatic solvents, Lewis bases, or aluminum compounds.

In carrying out the processes of this invention it is preferred to use alkali metals in the form of finely divided dispersions in an inert hydrocarbon medium such as a light mineral oil, a naphthenic hydrocarbon, heptane, octane, or methylcyclohexane, and dispersing agents and stabilizers which are generally used in preparing dispersions of this sort. Dispersant media are generally washed from the alkali metal before use but may be used as the solvent for reaction in those cases where no dispersing agent or stabilizer is employed.

Alkali metals contemplated in our invention are lithium, sodium, and potassium, and most preferably sodium metal because of the combination of its low cost and high reactivity.

Solvents suitable for use in the processes of this invention may be saturated acyclic hydrocarbons such as isopentane, n-pentane, n-hexane, n-heptane, or saturated cyclic hydrocarbons such as cyclohexane or methylcyclohexane or mixtures thereof. Aromatic hydrocarbons such as benzene or toluene and Lewis bases such as tertiary amines or ethers may also be employed, although in certain applications such as in the preparation of Ziegler-Natta catalysts for olefin polymerization such solvents are generally not desirable.

Process (a) of this invention involves addition of sodium trialkylmagnesiate dissolved in a hydrocarbon medium to a dialkylmagnesium-magnesium chloride slurry in a hydrocarbon medium with subsequent heating of the reaction mixture for 1-3 hours. The sodium trialkylmagnesiate solutions can be prepared by simultaneously adding to a stirred dispersion of an alkali metal in an inert liquid hydrocarbon solvent a soluble dialkylmagnesium compound and a 2-alkyl substituted $C_4$-$C_{18}$ primary alkyl halide, as disclosed in U.S. Pat. No. 4,678,614, incorporated here for reference.

In addition to the method shown in the above cited reference, sodium trialkylmagnesiates may also be prepared by reaction of alkyl halides with sodium metal in finely divided form in the presence of the products of the reaction of magnesium metal with an alkyl halide, i.e., dialkylmagnesium plus magnesium halide according to the following equation:

$$4 RCl + 8 Na + MgR'R^2 + MgCl_2 \rightarrow 2 NaMgRR'R^2 + 6 NaCl \quad (4)$$

It is preferable to add the dialkylmagnesium plus magnesium halide mixture to the sodium dispersion in hydrocarbon solvent at the same time the alkyl chloride is added in order to minimize reduction.

Thus, for example a di-n-butylmagnesium-magnesium chloride mixture previously prepared in methylcyclohexane at reflux from magnesium metal and n-butyl chloride, is added gradually to a finely divided dispersion of sodium metal in cyclohexane, while simultaneously adding 2-ethylhexyl chloride to the dispersion from a dropping funnel. The reaction temperature is kept below 35° C. After filtration a clear solution of sodium n-butyl-, bis-(2-ethylhexyl)magnesiate (0.9 normal) is obtained.

Sodium trialkylmagnesiates used in the practice of the present process (a) can vary widely in composition but are preferably soluble in the hydrocarbon solvents in which they are prepared, so that their solutions may be readily separated from by-product salts. Thus, for example, one may employ as reactants for preformed magnesium chloride/dialkylmagnesium mixtures such sodium trialkylmagnesiates as sodium n-butyl-n-octyl-2-ethylhexylmagnesiate, sodium n-butyl-sec-butyl-2-ethylhexylmagnesiate, sodium n-butyl-sec-butyl-n-hexylmagnesiate, sodium ethyl-n-butyl-2-ethylhexylmagnesiate, sodium n-butyl-n-octyl-2-methylpentylmagnesiate, sodium n-hexyl-n-octyl-2-ethylbutylmagnesiate, sodium butyl-hexyloctylmagnesiate, sodium n-butyl-bis-(2ethylhexyl)magnesiate and the like. It is not necessary for three different groups to be present, only that the stoichiometry correspond to three alkyl groups per mole of $NaMgR_3$.

If a sodium trialkylmagnesiate possessing a Na/Mg ratio higher than 1.0 is employed then the stoichiometry in $Na_xMgR_aR'_bR^2_c$ corresponds to $a+b+c=x+2$.

The dialkylmagnesium-magnesium chloride slurry in hydrocarbon solvent employed in the reaction should contain sufficient chloride in the magnesium chloride to react with all of the sodium in the sodium trialkylmagnesiate. Generally, one employs a 20–30% excess of magnesium chloride to ensure complete reaction. Molar ratios of sodium trialkylmagnesiate to magnesium chloride in the dialkylmagnesium/magnesium chloride mixture can vary from 1-2, but generally should preferably be in the range of 1.5-1.8.

Dialkylmagnesium compounds generated from magnesium metal and containing the magnesium chloride by-product of reaction may vary widely in composition in regard to alkyl group substitution. Examples of such dialkylmagnesium compounds include diethylmagnesium, n-butylethylmagnesium, di-n-butylmagnesium, di-n-hexylmagnesium, n-butyl-, n-octylmagnesium, methyl-, isoamylmagnesium, and mixtures thereof.

The reaction between said dialkylmagnesium-magnesium chloride mixtures and said sodium trialkylmagnesiate may be carried out at temperatures from well below 0° C. to about the boiling point of the solvent. However, although the addition step may be carried out at 25°-50°, an additional post-addition heating at 70°-90° for 1-3 hours is generally required to complete the reaction.

Good agitation should be maintained throughout the addition to ensure adequate contact with the reactants. Generally, the dialkylmagnesium compounds are generated in a separate step as part of the inventive procedure and may or may not contain by-product magnesium chloride. Generally, it is preferred that they do contain such magnesium chloride. However, in place of the by-product magnesium chloride described above, it is also within the scope of the invention to utilize other forms of highly active anhydrous magnesium chloride, although it is generally most convenient to utilize the magnesium chloride generated as a by-product of the reaction of magnesium metal with an alkyl halide in a hydrocarbon medium. This latter magnesium chloride is variously described as being "free" or "bound" to the dialkylmagnesium compound ($R_2Mg \cdot MgCl_2$) but is generally not considered to be in the form of "RMgCl" in hydrocarbon media containing no Lewis base.

As mentioned previously alkyl groups may be chosen over a wide range so as to impart superior solution properties to the resultant dialkylmagnesium compounds. Such properties include low viscosity, high solubility over a wide range of temperatures, and high thermal stability, i.e., resistance to thermal degradation. Much of this technology is known to the art. However, it has now been found possible to improve solution properties still further by incorporation of specific alkyl groups by means of the corresponding alkylsodium compounds in the form of sodium trialkylmagnesiates. Many of these particular groups cannot be incorporated through the use of the corresponding dialkylmagnesium compounds, since they are not formed by direct reaction of magnesium metal and the corresponding alkyl chlorides.

Such specific alkyl chlorides useful in the present invention are 2-alkyl-substituted chlorides as, for example, 2-methylbutyl chloride, 2-ethylbutyl chloride, 2-methylpentyl chloride, and 2-ethylhexyl chloride. Corresponding alkyl bromides may be used, but these are more costly and generally less commercially available than the chlorides. Incorporation of these groups into the desired dialkylmagnesium compounds by means of the reaction of sodium trialkylmagnesiates containing such groups with dialkylmagnesium-magnesium chloride mixture generally imparts a lower viscosity or an improved resistance to thermal degradation as compared to dialkylmagnesium compounds known to the art such as n-butyl-n-octyl magnesium, n-butylethyl magnesium, and n-butyl-sec-butylmagnesium. Thus, for example, incorporation of the 2-ethylhexyl group into a dialkylmagnesium compound by the process of our invention generally allows separation of its solutions in hydrocarbon solvents from by-product salts without the necessity of adding aluminum alkyls to lower their viscosity. Generally, equivalent viscosities to other commercially available dialkylmagnesium solutions in hydrocarbon solvents can be achieved with the use of significantly less aluminum alkyl than is used in said commercial solutions; or, if equivalent amount(s) of aluminum alkyls are utilized, significantly lower viscosities are achieved at equivalent Mg concentrations.

Improved resistance to thermal degradation is imparted by the presence of 2-alkylsubstituted primary alkyl groups in the novel dialkylmagnesium compounds as compared to dialkylmagnesium compounds containing 1-alkylsubstituted (secondary or tertiary) alkyl groups, such as n-butyl-, sec-butylmagnesium.

However, it is also within the scope of this invention to employ mixtures of 2-alkyl-substituted chlorides with other alkyl chlorides such as 2-ethylhexyl chloride for reaction with sodium metal to form the intermediate sodium trialkylmagnesiate such as, for example, ethyl chloride, n-butyl chloride, n-hexyl chloride, n-octyl chloride, sec-butyl chloride, isopropyl chloride, isobutyl chloride, tert-butyl chloride, and isoamyl chloride.

After reaction of the sodium trialkylmagnesiate with the dialkylmagnesium-magnesium chloride mixture, part of the resulting desired solution of novel dialkylmagnesium compounds (after separation from by-product salts) may be recycled to act as "carrier" for the alkylsodium, i.e., to reform sodium trialkylmagnesiate and then, by reaction with fresh dialkylmagnesium/magnesium chloride, to form more novel dialkylmagnesium compound. The novel dialkylmagnesium product may contain a number of different alkyl groups totalling two groups per Mg. Thus, for example, one may obtain n-butyl-ethyl-2-ethylhexyl-magnesium, n-butyl-n-octyl-2-ethylhexylmagnesium, n-butyl-sec-butyl-n-octyl-2-ethylhexylmagnesium, n-hexyl-2-ethylhexylmagnesium, n-butyl-ethyl-2-ethylbutylmagnesium, n-octyl-2-ethylbutylmagnesium, n-butyl-sec-butylisobutylmagnesium, n-butyl-2-methylpentylmagnesium, and the like.

Thus, for example, in the first step of such a cyclic process, a hydrocarbon solution containing an equilibrated alkyl-interchanged mixture of 0.1 mole of bis-2-ethylhexylmagnesium and 0.3 mole of $(n\text{-butyl})_{1.5}(n\text{-octyl})_{0.5}$ magnesium, is obtained by reacting 0.2 moles of sodium n-butyl-, n-octyl-, 2-ethylhexylmagnesiate $(NaMg(n\text{-}Bu)_{1.5}(n\text{-octyl})_{0.5}(2\text{ethylhexyl})_{1.0})$ with 0.1 moles of $(n\text{-butyl})_{1.5}(n\text{-octyl})_{0.5}$magnesium and 0.125 moles of by-product magnesium chloride, followed by filtration to remove sodium and magnesium chloride salts. A solution 0.63 molar in magnesium and essentially free of sodium is obtained, and is next converted to a solution of sodium trialkylmagnesiate by reaction with an equivalent of 2-ethylhexylsodium prepared in the presence of the dialkylmagnesium according to U.S. Pat. No. 4,678,614.

In the second step of the said cyclic process, 0.2 moles of the resulting solution of $[2\text{-ethylhexylsodium}]_{1.0}[\text{bis-2-ethylhexylmagnesiumbutyl}]_{0.25}[(n\text{-butyl})_{1.5}(n\text{-octyl})_{0.5}\text{magnesium}]_{0.75}$ is again reacted with a mixture of 0.1 moles of $(n\text{-butyl})_{1.5}(n\text{-octyl})_{0.5}$ magnesium and 0.125 moles of by-product magnesium chloride, followed by filtration to separate the product containing solution from sodium and magnesium salts. A hydrocarbon solution, 0.46 molar in magnesium and essentially free of sodium is obtained, with an approximate ratio of n-butyl/2-ethylhexyl/n-octyl groups of 3:2.4:1.

In another embodiment [process (b)] of the invention sodium alkyls are prepared in the presence of dialkylmagnesium-magnesium chloride mixtures (generated in a prior step by the reaction between magnesium metal and an alkyl halide) resulting in a simultaneous reaction of the resulting sodium trialkylmagnesiates with contained magnesium chloride to yield novel hydrocarbon soluble dialkylmagnesium compounds according to Equation (3). This process is generally preferably carried out by adding a finely divided dispersion of sodium metal in a hydrocarbon solvent to a previously prepared mixture of dialkylmagnesium compound and by-product magnesium chloride (derived from magnesium metal and an alkyl halide) and then gradually adding the desired alkyl halide reactant to the agitated mixture. Thus, for example, a 2-alkyl substituted alkyl halide, such as 2-ethylhexylchloride, is gradually added to an agitated mixture of finely divided sodium, a dialkylmagnesium compound (such as n-butyl-n-octylmagnesium) and magnesium chloride in a hydrocarbon medium, the reaction temperature being maintained in the range of 30°–40° C. After reaction is complete, the desired solution of dialkylagnesium compounds is separated by filtration. It is also possible to simultaneously add the dialkylmagnesium-magnesium chloride mixture (e.g., previously generated from magnesium metal and alkyl halide) along with the reactant alkyl halide, preferably a 2-alkyl-substituted alkyl halide, to the slurry of finely divided sodium metal in a hydrocarbon medium.

Generally, the ratio of sodium to magnesium compounds in this reaction is maintained at approximately two. Thus, for example, in the following equation wherein R is a 2-ethylhexyl group, $$4\,Na + 2Rcl + MgR'_2 + MgCl_2 \rightarrow 2\,RMg(R') + 4\,NaCl$$

However, as described above for process (a), an excess of magnesium chloride over dialkylmagnesium-complexed sodium alkyl is desirable. The 2-alkyl substituted alkyl halides used for reaction with sodium metal dispersion in process (b) are the same as those described above for process (a), and mixtures of these with other alkyl halides can be employed.

The process of the invention may be extended to the preparation of well-known commercially-produced dialkylmagnesium compounds such as, for example n-butylethylmagnesium, n-butyl-n-octylmagnesium, and n-butyl-sec-butylmagnesium by gradual addition of ethyl chloride, n-octyl chloride, and sec-butyl chloride, respectively, to a mixture of sodium dispersion and di-n-butylmagnesium in the presence of its by-product magnesium chloride salt contained in a hydrocarbon solvent medium.

Thus, for example n-butyl-n-octylmagnesium is prepared by the dropwise addition of n-octylchloride to a mixture of sodium dispersion, di-n-butylmagnesium, and magnesium chloride.

Dialkylmagnesiums in the dialkylmagnesium-magnesium chloride mixtures may vary widely in composition, as described above for process (a).

The following examples further illustrate various aspects of the invention, show how the process may be practiced, and describe various novel soluble dialkylmagnesium compounds in accordance with the invention. Although specific procedures and reactants are described in these examples, it will be understood that these are provided for purposes of illustration and are not to be regarded as limiting the scope of the present invention. Persons skilled in the art will recognize that other novel dialkylmagnesium compounds can be made pursuant to this invention.

EXAMPLE 1

Preparation of n-Butyl-n-Octyl-2-Ethylhexylmagnesium-Process (a)

A. First Step of Cyclic Process

A mixture of 7.29 g (0.30 moles) of magnesium powder ($-100$ mesh) and 175 ml of Union Oil Co. Special Naphtholite 66/3 Solvent (a mixture of cyclic and acyclic saturated hydrocarbons with b.p.=133° C.) was conditioned by stirring with 3 ml of a 0.36M di-n-hexylmagnesium solution and heated to reflux. Heating was discontinued, and the slow (dropwise) addition of a mixture of 19.6 ml (0.1875 moles) of n-butyl chloride and 10.4 ml (0.0625 moles) of n-octyl chloride begun, maintaining the reflux throughout the addition. The addition of halides was complete in one half hour, after which the reaction mixture was heated (reflux) and stirred for about two hours.

After cooling the reaction mixture to 60° C., 435 ml (0.20 moles) of a preformed solution of sodium n-butyl-, n-octyl-, 2-ethylhexylmagnesiate (NaMg(n-Bu)$_{1.5}$(n-Oct)$_{0.5}$(2-EtHex)$_{1.0}$) in heptane[1] was added as rapidly as possible. No heat was given off during this addition, and the temperature of the reaction mass fell to 38.4° C. The solution was heated to 50° C. for three hours, then allowed to cool and settle overnight. A sample of the clear supernatant solution was analyzed for sodium and magnesium content (Mg=0.53M, Na=0.13M; Mg/Na=4.1). The reaction mixture was again heated, this time to 65°–70° for a two hour period and then to about 85° C. for two hours. After cooling, analysis of the super natant solution showed the following values: Mg=0.63M, Na=0.01M, Al=0.008M. Essentially, all of the sodium trialkylmagnesiate was converted to dialkylmagnesium.

[1] Prepared via procedure in U.S. Pat. No. 4,678,614 from BOMAG-A (n-butyl-n-octylmagnesium, Schering, A.G.) 2-ethylhexyl chloride, and sodium dispersion.

The reaction mixture was filtered to give a clear, slightly yellow-colored, slightly viscous solution (viscosity similar to mineral oil). The solids were washed with a small amount of heptane and the washing combined with the main filtrate to give 438 g (603 ml) of a 1.09N solution (0.66 equivalents, 78% yield based on starting halide in Mg reaction and NaMgR$_3$). The solution contained Mg=0.54M, Na=0.0001M, and Al=0.006M (1 mole % Al on Mg) and possessed a final solution viscosity of 11.5 cps (40°). This can be compared to a solution viscosity of 12.5 cps (40°) for butyloctylmagnesium (BOMAG-A) (Mg=0.87M) containing 3 mole % Al on Mg, a significant reduction in the Al requirement.

B. Second Step of Cyclic Process

The product of Step A above was first converted to a sodium trialkylmagnesiate by reaction of it with 2-ethylhexylsodium.

To 14 grams (0.61 grams atoms) of sodium dispersion in 190 ml of heptane is gradually added (1.3 hours) 2-ethylhexyl chloride (36.8 ml, 0.218 moles) and the n-butyl-, n-octyl-, 2-ethylhexylmagnesium solution (364 ml, 0.20 moles), prepared in Step A above. The temperature is kept between about 30°–40° throughout the addition. After stirring an additional 2.5 hours, the mixture is filtered to give 597 ml of a pale yellow solution with magnesium and sodium concentrations of 0.32M and 0.30M, respectively, and a total base (alkalinity) concentration of 0.95N (0.566 eq).

The above solution is added to the dialkylmagnesium-magnesium chloride reaction product of 0.30 g atoms of magnesium powder, 19.6 ml (0.1875 moles) n-butylchloride, and 1.04 ml (0.0625 moles) n-octyl chloride in 175 ml of SN 66/3 solvent at about 65° C. as described in Step A above. The temperature of the reaction mass drops to 53° C. during the addition of the sodium trialkylmagnesiate solution to the mixture of dialkylmagnesium and magnesium chloride. The reaction mass is heated to 85° C. for two hours, then analyzed for solution Mg and total alkalinity (T.B.): T.B.=1.0N, Mg=0.495M. Essentially, all of the NaMgR$_3$ reacts. The reaction mass is filtered readily (25 minutes) at 60° C. and 6–8 psi pressure to give an almost water-white solution (796 ml, 573 g).

Analysis gives the following significant values:
T.B.=0.89N
Mg=0.46M
Na=0.0003M (0.06 mole % on Mg)
Al=0.0027M (0.6 mole % on Mg)
Viscosity=20.1 cps (40° C.)

Again, the viscosity of the resulting solution was low, even in the presence of only 0.6 mole % Al on Mg, as compared to the generally employed 2–3 mole % of Al.

A portion (195 ml) of the above solution was concentrated by vacuum stripping (ROTOVAP) to 1.09M (3.7 wt. % Mg). Addition of 3 mole % triisobutylaluminum decreased the viscosity to below 10 cps (40° C.).

Analysis of a commercial solution of a 20 wt. % n-butyl-, n-octylmagnesium (2.9 wt. % Mg) in heptane shows a viscosity of 12.7 cps (40° C.), a value higher than that for the inventive product solution, but at a significantly lower magnesium concentration. This shows the viscosity lowering effect of the presence of the 2-ethylhexyl group in the dialkylmagnesium compound.

EXAMPLE 2

Preparation of n-Butyl-2-Ethylhexylmagnesium

This example shows the preparation of dialkylmagnesium compound using 2-ethylhexylsodium and a di-n-butylmagnesium-magnesium chloride mixture.

To a reaction mixture derived by cooking magnesium metal powder (0.30 g atoms) and n-butyl chloride (0.25 moles) together in 175 ml refluxing heptane was added a solution of 2-ethylhexylsodium (310 ml of 0.65N conc.) in heptane,[2] the temperature of reaction not exceeding 42° C. On filtration of the reaction mixture, a solution which was 0.64N in total alkalinity and 0.34M in Mg was obtained. The solution was concentrated to 0.64M (2.2 wt. % Mg) in Mg (Na=0.0025M). Some precipitation of solids occurred in the solution on standing overnight (Mg=0.55M). Sufficient triisobutylaluminum in hexane solution was added to give a final Al concentration corresponding to 3 mole % on the total Mg. All solids immediately dissolved and a very fluid solution resulted. The viscosity of this solution was found to be only 1.25 cps (40° ), a significantly lower value than that listed for a commercial n-butylethylmagnesium in heptane solution at the same magnesium concentration (about 15 cps). Again, the viscosity lowering effect of the 2-ethylhexyl group, as well as its solubilizing properties, was noted. (Di-n-butylmagnesium alone possesses only a very low order [<0.2M] of solubility in hydrocarbon solvents.)

[2] The yield of 2-ethylhexylsodium is 65%.

EXAMPLE 3

Preparation of n-Butyl-, n-Octyl-, 2-Ethylhexylmagnesium

Example 2 was repeated using, instead of n-butylchloride alone, a 90/10 n-butylchloride-n-octylchloride feed for the Mg metal reaction. Also, methylcyclohexane was used in place of heptane as the solvent for the 2-ethylhexylsodium preparation. A low yield (48%) of 2-ethylhexylsodium was obtained.

After filtration of the product mixture obtained by adding the 2-ethylhexylsodium solution to the magnesium metal-mixed alkyl halide reaction product, the filtrate was found to be 0.69N in total alkalinity and 0.35M in Mg. Sufficient triisobutylaluminum (TIBAL) was added to give an Al concentration on Mg of 2 mole %. The solution was concentrated to give a solution 1.04M (3.5 wt. % Mg) in magnesium, 0.02M in aluminum, and 0.0076M in chloride. The viscosity of the solution was found to be 11.3 cps (40°) comparable to commercially available solutions, but at a higher contained magnesium concentration.

EXAMPLE 4

Preparation of n-Butyl-, n-Octyl-, 2-Ethylhexylmagnesium-Process (b)

To a reaction mixture derived by reacting magnesium metal powder (0.25 gram atoms) with a mixture of n-butylchloride (0.225 moles) and n-octyl chloride (0.025 moles) in refluxing heptane (175 ml) then cooling to 40°, was added a sodium (0.55 gram atoms) dispersion in heptane (100 ml). To this mixture was gradually added 2-ethylhexyl chloride (0.25 moles) with stirring, keeping the temperature generally between 30°–40°. After completion of the 2-ethylhexyl chloride addition, the reaction mixture was heated to 80° C. for one hour, then cooled to room temperature. After filtration to remove unreacted metals and metal salts, a clear, colorless, somewhat viscous solution having a Mg concentration of 0.64M was obtained (Total Alkalinity=1.25N). After washing the solids with heptane, the Mg concentration was 0.52M and the yield of recovered dialkylmagnesium in solution is 74% (based on all alkyl halides used).

A 0.6M solution of this product showed the following viscosity values at 0%, 1%, 2%, and 3% (mole basis) of added triisobutylaluminum (TIBAL).

| Mole % Added TIBAL | Viscosity (cps, 35° C.) |
| --- | --- |
| 0 | 32 |
| 1 | 8.2 |
| 2 | 4.8 |
| 3 | 3.4 |

The viscosity of the untreated (0% Al) product (32 cps at 35° C.) was considerably less than that of n-butylethylmagnesium, (850 cps@35° C.) another commonly used magnesium alkyl, tested at the same concentration in heptane and containing no viscosity-reducing agent, as shown in U.S. Pat. No. 4,547,477. This latter product is generally sold commercially with sufficient added aluminum (2–3 mole % on Mg) to bring its viscosity down to 15 cps or less (no other viscosity modifying additive being present). The product of this example requires only approximately 0.5 mole % Al to achieve such a viscosity at the same contained magnesium concentration and the solution is fluid enough even with no added aluminum. The viscosity lowering effect of the presence of the 2-ethylhexyl group in the dialkylmagnesium compound is demonstrated.

EXAMPLE 5

Preparation of n-Butyl-, n-Hexyl-, 2-Ethylhexylmagnesium-Process (a)

1. Preparation of di-n-Butylmagnesium-Magnesium Chloride

A volume of 23.7 ml (20.8 g, 0.225 moles) of n-butyl chloride was added gradually to a slurry of 6.8 g (0.25 g moles) of magnesium powder in 175 ml of methylcyclohexane at reflux (100° C.). After addition was complete, the mixture was refluxed for an additional 1-2 hours and allowed to cool to room temperature.

2. Preparation of Sodium n-Butyl-, bis-(2-Ethylhexyl) Magnesiate

A weight of 62 grams of sodium dispersion (40 wt. % in mineral oil containing 1.08 g atom of sodium metal) was mixed with 200 ml of cyclohexane in a one liter flask. While stirring, reaction was initiated by addition of 8 drops of a volume of 76 ml of 2-ethylhexyl chloride (EHC). After about 10 ml of EHC was added to the reaction mixture, reaction mixture (1) above was added via syringe (10 gauge needle) simultaneously while continuing addition of the EHC, over a 26 minute period, keeping the temperature below 35° C. The reaction mixture was stirred for another hour and filtered. A volume of 564 ml of a clear, light greenish-yellow filtrate was obtained with the following assay: Total alkalinity—0.90 Normal, Magnesium (titrated)—0.28 Molar, Sodium (flame)—0.32 Molar. The recovered yield of sodium trialkylmagnesium was 74% based on combined initial n-butyl chloride and 2-ethylhexyl chloride.

3. Preparation of n-Butyl-, n-Hexyl-, 2-Ethylhexylmagnesium

A portion of the sodium n-butyl-, 2-ethylhexylmagnesiate (0.10 moles) solution from (2) above was added rapidly while stirring to a mixture containing 0.05 moles of di-n-hexylmagnesium and 0.07 moles of magnesium chloride. After the addition was complete, the reaction mixture was heated for two to three hours at 85° C., cooled, and filtered to give a clear fluid, colorless solution of n-butyl-, n-hexyl-, 2-ethylhexylmagnesium.

We claim:

1. A low viscosity dialkylmagnesium composition consisting essentially of a compound of the formula $$MgR_aR^1_bR^2_cR^3_dR^4_e$$

wherein
a=0.5 to 1.9; b, c, d, and e=0.1 to 1.5; and
a+b+c+d+e=2
R is a 2-alkyl substituted primary alkyl group and $R^1$, $R^2$, $R^3$, and $R^4$ are $C_2$–$C_{18}$ hydrocarbyl groups which may be the same or different, said dialkylmagnesium being in the form of a solution in a liquid aliphatic and/or cycloaliphatic solvent.

2. The low viscosity dialkylmagnesium composition of claim 1 in which R is 2-ethylhexyl and $R^1$, $R^2$, $R^3$, and $R^4$ are a mixture of n-butyl and n-octyl groups.

3. The low viscosity dialkylmagnesium composition of claim 1 further consisting of up to 2 mole percent of a trialkyl aluminum compound.

* * * * *